United States Patent [19]

Schimion et al.

[11] Patent Number: 4,801,863
[45] Date of Patent: Jan. 31, 1989

[54] APPARATUS FOR MONITORING THE MIXING RELATIONSHIP OF TWO LIQUIDS

[75] Inventors: Werner Schimion; Gerhard Kusche; Klaus Reucker, all of Hilchenbach, Fed. Rep. of Germany

[73] Assignee: SMS Schloemann-Siemag AG

[21] Appl. No.: 858,392

[22] Filed: May 1, 1986

[30] Foreign Application Priority Data

May 11, 1985 [DE] Fed. Rep. of Germany ....... 3517065

[51] Int. Cl.$^4$ ............................................ G01N 27/22
[52] U.S. Cl. ............................. 324/61 R; 73/61.1 R
[58] Field of Search ................. 324/61 R, 61 P, 60 C; 73/61.1 R

[56] References Cited

U.S. PATENT DOCUMENTS 4,559,493 12/1985 Goldberg et al. ................ 324/61 R Primary Examiner—A. D. Pellinen
Assistant Examiner—Leon K Foller
Attorney, Agent, or Firm—Toren, McGeady & Associates

[57] ABSTRACT

Apparatus for enabling continuous monitoring of a mixture ratio of two different liquids as well as to limit it to those mixture amounts which are drawn off at a particular time for the purpose of being used which includes a receptacle filled by a liquid or through which the liquid flows. The receptacle comprises two electrodes insulated from each other and located opposite each other at which a capacitance measuring device determining the respectively occurring capacitance is connected. The dielectric constants of the components of the mixture which differ in many mixtures, for instance, in an oil-water mixture, permit, because of the fixed dimension of the constituted condenser, the determination of the composition of the mixture by means of the respectively existing dielectric constant so that, for instance, harmful water penetrating into oil systems provided for lubrication can be determined in small amounts and can trigger appropriate warning signals.

7 Claims, 4 Drawing Sheets

APPARATUS FOR MONITORING THE MIXING RELATIONSHIP OF TWO LIQUIDS

The present invention relates to apparatus for monitoring the mixing relationship or ratio of two different liquids, in particular, those with considerably differing dielectric constants.

In actual practice, liquid mixtures are often utilized under circumstances where a first liquid is mixed with a second, undesired liquid. In many cases, it is essential to determine the concentration ratio of the liquids for keeping a desired mixture ratio constant and for monitoring a critical mixture ratio in the case of undesired admixtures.

An essential application area of this type is, for example, the monitoring of oil. In cases where oil returning from motors, machine tools, rolling mills, or the like, is collected and purified so as to be used again, the danger always exists that apart from other foreign bodies, the oil absorbs water in the course of its circulation which impairs its lubricity. In order to assure the required lubricity, it is therefore required to control the water absorption by the oil.

It has been found that drawing and analyzing test specimens is not only difficult and costly, but that the determined water content is a function of the location from which the specimen has been drawn, and an increased water content indeed permits statements as to the reduction of the lubricity, but generally does not show the path on which the water has reached the oil. Monitoring on the basis of sporadically drawn specimens furthermore yields considerable delays between the unacceptable rise of the water content and discovery of same since, to start off with, the specimens are drawn off periodically and then the respective examination requires time.

The invention, therefore, proceeds from the need to create an arrangement in accordance with the species by means of which, appropriately, only the liquid which is to be used or drawn off is analyzed as to its concentration, and requires as continuous a determination as possible with a small expenditure of energy.

SUMMARY OF THE INVENTION

The present invention is embodied in apparatus comprising a receptacle which either contains the liquid to be examined or through which, the liquid to be examined circulates continuously and which is desiged as a condenser by arrangement of two electrodes opposite each other. The capacitance of the electrodes can be continuously monitored by simple means. Here, the capacitance to be measured is, on the one hand, determined by the dimensions of the receptacle (or container) or electrodes and their spacing which indeed remain constant and do not enter into the ensuing determination. In addition, however, the capacity depends on the dielectric constant of the dielectric substance existing between the electrodes and thus of the dielectric constant of the liquid introduced into or circulating through the container. Excellent conditions exist in the determination of the concentration of water admixed to the oils, because the dielectric constant of the usual lubricating oils as well as many other hydrocarbons lies in the range of 2.2, while substances foreign to oil in part have a strongly deviating dielectric constant. The often occurring water is clearly recognized already in minor traces by its high dielectric constant of 80 and thus is easily detected. The utilization of a container through which liquid is circulating in addition with a capacitance measuring device results in a continuously running check, which makes the exceeding of still allowable admixtures strikingly and clearly recognizable by triggering of optical and/or acoustic signals.

The various features of novelty which characterize the invention are pointed out with particularity in the claims annexed to and forming a part of this disclosure. For a better understanding of the invention, its operating advantages and specific objectives attained by its use, reference should be had to the drawings and descriptive matter in which there are illustrated and described the preferred embodiments of the invention.

DETAILED DESCRIPTION OF THE PREFERRED EMBODIMENTS

Figure 1:
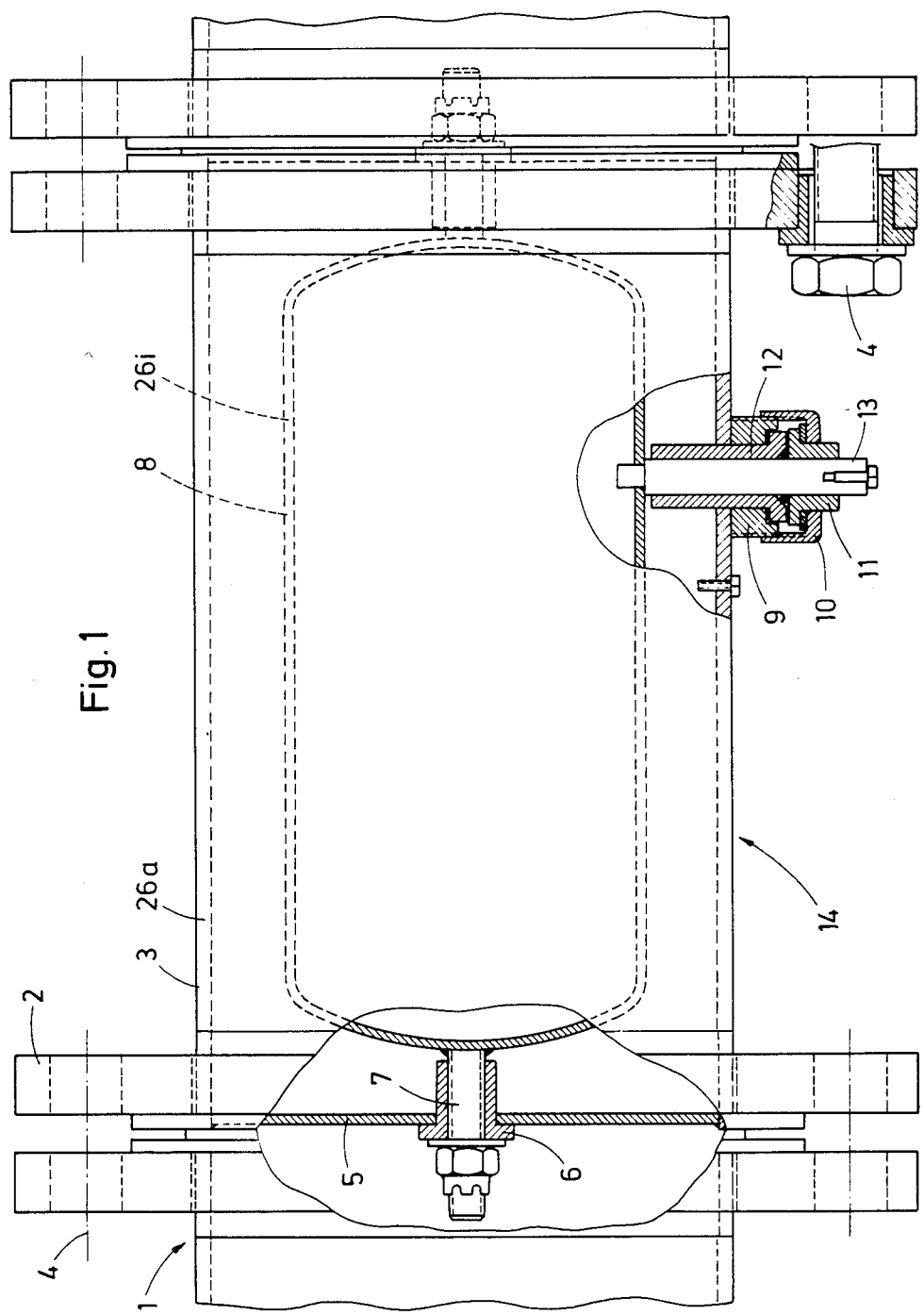
FIG. 1 is a longitudinal section schematically showing the basic elements of the invention.

Referring now to the drawings, and particularly to FIG. 1, there is shown apparatus in accordance with a preferred embodiment of the invention comprising a pipe stub 3 having flanges 2 on both sides attached by means of screws 4 into a longitudinal section of a piece of piping 1 truncated on both sides, whereby the pipe stub 3 is electrically separated from the piping 1 by utilization of insulating sealing disks and insulating bushings encasing the screws 4. Flanges 2 of the pipe stub 3 are equipped with centering disks 5 comprising fluid passage openings, and having central bores into which insulating bushings 6 are inserted. Bolts 7 provided in the center at both ends of a cylinder member 8 extend through the bushings 6. Furthermore, at its outer surface, the pipe stub 3 comprises a threaded stub 9 in which a seal 11 as well as an insulating bushing 12 are clamped by means of a union nut 10 through which a connecting bolt 13 extends. Thus, a receptacle 14 is created which is also penetrated by the same liquid which flows through the pipeline 1, whereby the liquid enters and exits the receptacle 14 through penetrations in the centering disks 5 and circulates within the receptacle through the pipe-shaped space formed between the outer surface of the cylindrical member 8 and the inner surface of the pipe stub 3. The insulated retention of the cylindrical member 8 due to the insulating bushings 6 and 12 allows its use as the inner electrode $26i$ which is connectable through the connection bolt 13, while the pipe stub 3 acts as the outer electrode $26a$ of the cylindrical condenser formed by the two electrodes. If the pipe stub 3 is installed so as to be insulated, it can be switched as a free backplate electrode. However, it is also possible to insert the pipe stub 3 into the pipeline 1 in a conducting manner and to utilize it as a grounded electrode.

Figure 2:
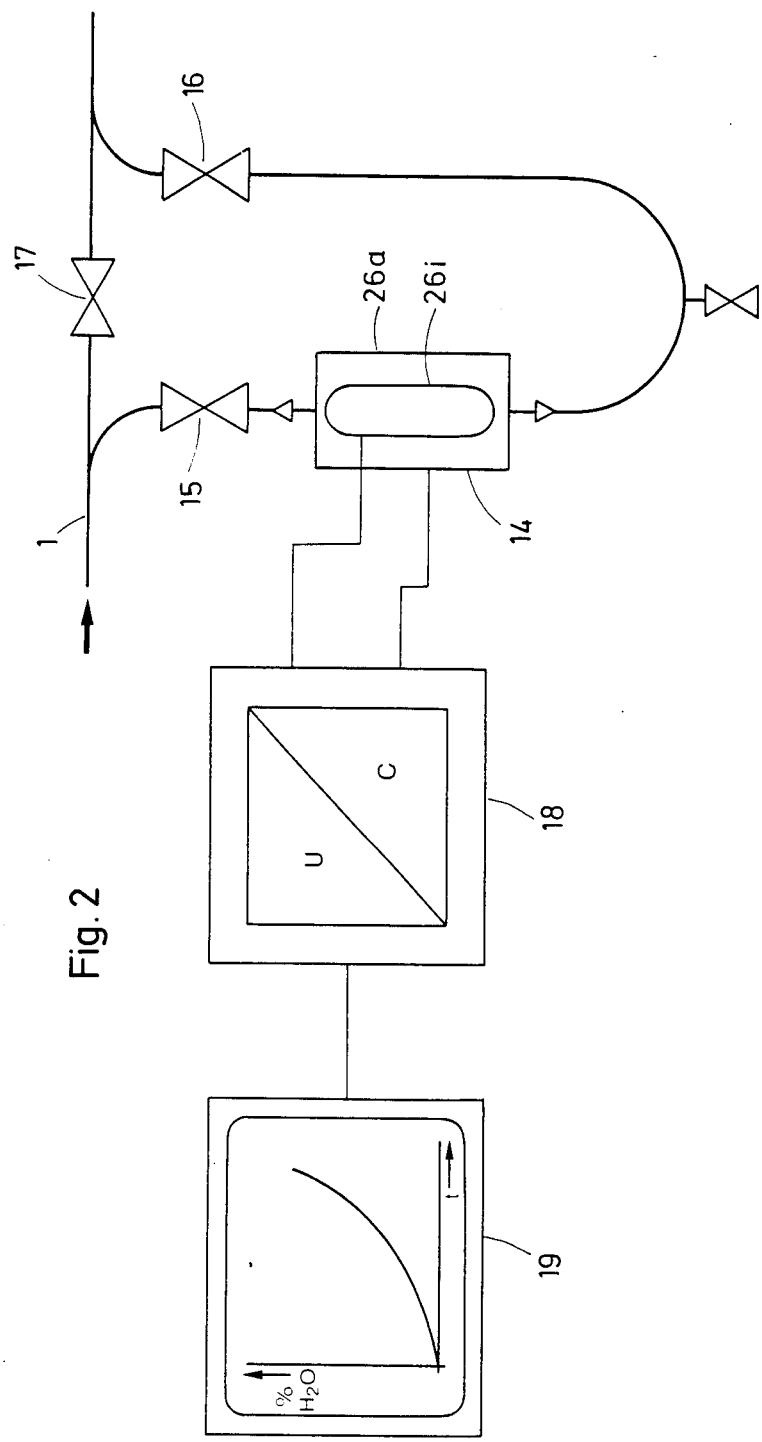
FIG. 2 is a schematic diagram showing an arrangement encased in a piece of piping which can be bridged over.

FIG. 2 schematically illustrates the layout of the measuring arrangement. In order to be able to maintain the receptacle 14, and possibly to enable it to be replaced or overhauled, it is inserted into a loop of the piping which can be blocked off by shutoff valves 15 and 16. In the course of the measuring process, the direct connection of the pipeline 1 is interrupted by means of a shutoff valve 17. The electrodes 26i and 26a of the receptacle 14 are connected with a capacitance measuring device 18 which transmits a voltage U corresponding but preferably proportional to the capacitance formed between the electrodes 26a and 26i to a display device 19. In the simplest case here, simple indicating instruments or even, in case of exceeding or dropping below the preset threshold, actuating contacts of, for instance, a relay are sufficient. A better overview is obtained and the chronological history can be presented, if recording measuring devices, for instance, dotted line recorders, plotters or such, are provided. Rapid observation results if a monitor connected with the storage device is utilized which records timewise successive capacitance values, so that a chronological variation of the capacitance can be ascertained.

If predetermined liquids are used, the determined capacitance represents a function of the concentration of a specific second and a specific first liquid, so that the indicating device does not have to be graduated in capacitance values, rather, directly into values corresponding to the concentration, for instance, in the percentage mixture ratio. Particularly favorable conditions result for the determination of water in carbohydrates, because these exhibit a relatively low dielectric capacitance with the water having a value which is about 35 times higher. Because of this, a linear curve for relatively low admixtures of water results. In case there is no admixture, the initial capacitance can be compensated here by an appropriate adjustment or a fixed compensation.

Figure 3:
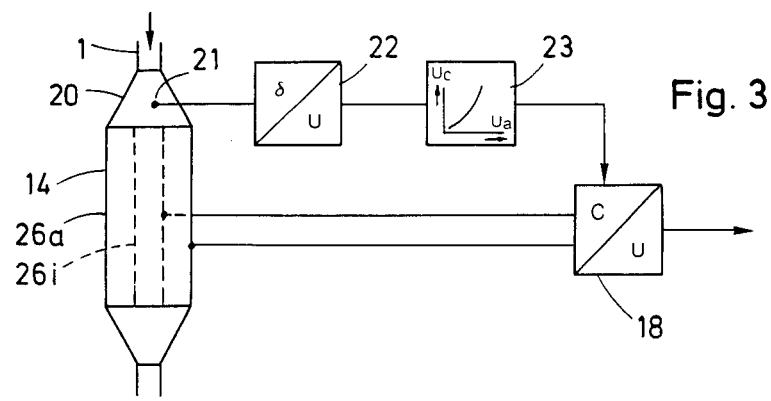
FIG. 3 is a schematic diagram showing a temperature compensated construction of the arrangement.

It has, however, been shown in practice that the dielectric constant of carbohydrates, for instance, oils, exhibits a non-negligible temperature variation. Here, an arrangement according to FIG. 3 has proved successful in which the electrodes 26a and 26i of the receptacle 14, through which the liquid to be monitored flows, are connected with a capacitance measuring device 18 to which an outside corrected voltage can be supplied.

In order to achieve an adaptation of the free cross section of the pipeline 1 to the useful flow cross section of the receptacle 14, transition cones 20 are provided on both sides of the receptacle 14. In the receptacle 14 or, as in the embodiment depicted, within one of the transition cones 20, a temperature sensor 21 of a temperature transmitter 22 is arranged which transmits a voltage corresponding to the determined temperature to a function display device 23, and thus corresponding to the predetermined function of the temperature change of the dielectric constant of the basic liquid triggers a correction voltage and corrects the temperature variation of the dielectric constant of the liquid within the capacitance measuring device 18. Therefore, the original voltage no longer in effect corresponds to the capacitance provided between the electrodes 26a and 26i, but rather to a capacitance that refers to a fixed temperature, and thus is able to indicate the mixture ratio independent of temperature.

Figure 4:
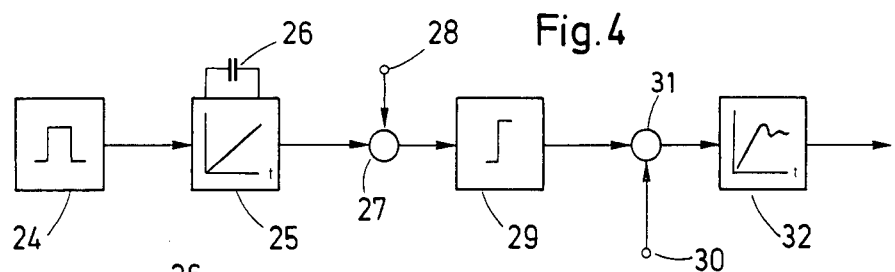
FIG. 4 is a schematic representation of an analog capacitance measuring device.

The possible construction of a capacitance measuring device is illustrated in FIG. 4. In its block diagram, a square wave signal generator 24 is depicted which controls an integrator 25, the steepness of its two flanks being determined by the capacitance of the electrodes 26 connected thereto. A reference voltage supplied through a connection 28 is superimposed in a connector 27 onto the resulting rising as well as falling voltage with obliquely extending flanks so that when a predetermined voltage threshold is exceeded, the conducting comparative circuit becomes conductive only during the segment of the symmetric, sawtooth-shaped voltage which is located above the threshold voltage. In the case of a steep rise and fall within the integrator 25, there result longer periods of conductivity than in the case of smaller steepness achieved under the influence of the capacitance of the electrodes 26, so that the length of the pulses furnished by the comparator 29 is primarily a measurement of the capacitance of the electrodes 26 of the receptacle 14 which corresponds to the dielectric constant of the mixed liquid and thus to the concentration. Here also, temperature variation of the dielectric constant is compensated by supplying the original voltage of a temperature transmitter or a function imager or display device 23 switched downstream of a temperature transmitter through the terminal 30. The difference of these voltages reaches a filter 32 through the link 31 equalizing the intermittent voltage and converting it into a direct current signal whose output voltage is supplied as a constant voltage to the indicating device 19 (not shown).

Capacitance measuring arrangements are, however, not limited to such a circuit acting in an analog manner. Thus, for instance, the capacitance generated between the electrode 26 can be switched parallel to the components determining the frequency, for instance, to the oscillating circuit of a generator, so that its frequency is determined by the capacitance of the receptacle 14. The evaluation can then be effected within the framework of the frequency measurement, for instance, by means of the flank of a downstream oscillating circuit. Evaluation can be simplified while maintaining the absolute frequency change if, by mixing with the frequency of a fixed generator, one converts to a lower frequency.

Finally, the arrangement in FIG. 4 can also be simplified by substituting a simple resistance-capacitance module in place of the integrator 25 whose capacity is essentially or large formed by the capacitance of the electrodes 26 of the receptacle 14. With this, the sawtooth-shaped voltage assumes the place of a straight line symmetrical flank of the voltage generated by the integrator, whose flank extends in accordance with an e-function, and whose steepness corresponds to the time constant of the charging or discharging paths.

Figure 5:
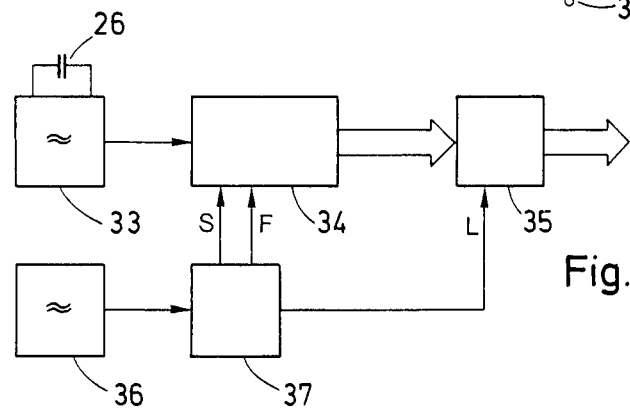
FIG. 5 is a block diagram of a digital capacitance measurement device.

An example of the digital capacitance measurement is explained with reference to FIG. 5. This block diagram shows a frequency generator 33 whose links determining the frequency include the capacitance of the electrodes 26. Thus, a frequency depending on their capacity is generated, and the periods of this frequency are counted in the counter 34 which transmits the result of its counting process accomplished at a predetermined interval and proceeding respectively from the fixed value periodically into an output memory 35 which controls a control or memory unit or indeed display devices respectively switched downstream.

For controlling this arrangement, a second reference generator 36 operating at a fixed frequency is provided which serves as a time transmitter for a control logic 37 which adjusts the counter 34 by means of signals S onto a predetermined value, releases the counting process with a signal F, and transmits through signals L at the end of an evaluation interval the resulting final value to the output memory from which it is further transmittable as a value representing the capacitance, or the dielectric constant, or the concentration.

Here also, appropriately, a temperature sensor is provided with a temperature transmitter switched downstream which effects temperature compensation. This can be caused by an additionally switched-in voltage-dependent capacitance influencing the frequency generator 33 as well as by other means additionally influencing its capacitance.

Figure 6:
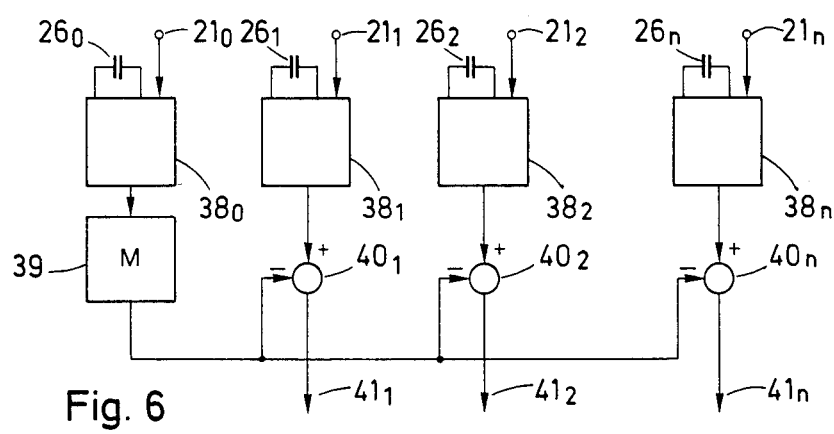
FIG. 6 is a schematic representation of an arrangement indicating a concentration rise occurring in individual legs.

In many cases, however, the interest may not be primarily in the measurement of a liquid flowing through the receptacle. In the case of oil circulation in rolling mills, for instance, the interest is not only in the undesirable rise of the water content, but also in where this additional share of water originates. A proven arrangement in this case is explained in its basic principles with reference to FIG. 6. Here, to start off with, receptacles not depicted and temperature compensated capacitance measuring devices 38 arranged downstream of these are, on the one hand, provided in the entire entrance of the roll stand oil and designated with the index 0, while with the indices 1 to n designated capacitance measuring devices $38_1$ to $38_n$ are provided for each of the return lines. The capacitance measuring devices are controlled respectively through the capacitance which exists between the electrodes 26 of the assigned receptacle, whereby the electrodes $26_0$ are part of the receptacle provided in the entrance, while the electrodes $26_1$ to $26_n$ belong to receptacles which are arranged in the individual return lines. The receptacles furthermore exhibit respective temperatures $21_0$ to $21_n$ which equally are respectively connected with capacitance measuring devices 38 and cause their temperature compensation. An average value generator 39 is arranged downstream of the capacitance measuring device $38_0$ provided in the entry which forms an average value out of the continuously determined dielectric constants or indications of concentration. This average value is supplied to the outputs of subtractors $40_1$ to $40_{10}$ arranged downstream of the remaining capacitance memory devices $38_1$ to $38_n$ so that the average value of the entrance area is subtracted from the entirety of the results generated from the return, and only signals representing the respective difference with respect to the average value appear at the outputs $41_1$ to $41_n$ of the subtractors 40. It is thus considerably simplified in larger plants to determine in case of occurring concentration changes in which of the return lines this changing concentration essentially occurs so that error sources or admixture points are easily localized.

Figure 7:
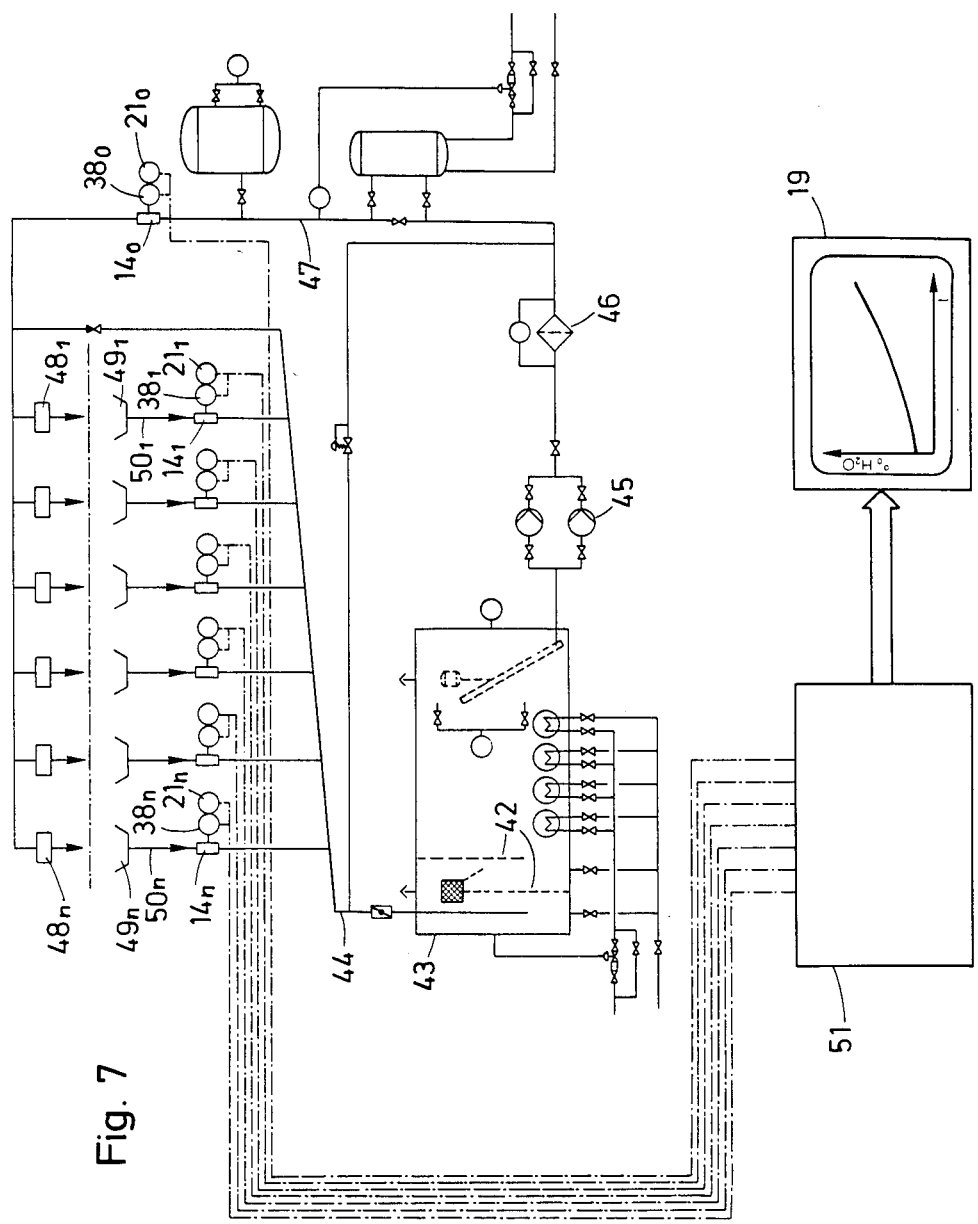
FIG. 7 is a schematic diagram showing the practical layout of an arrangement for monitoring the oil circulation in a rolling mill.

A practical application of the arrangement depicted in principle in FIG. 4 can be discerned from FIG. 7. Here, an oil container of an oil circulation system subdivided by partitions 42 into chambers is shown to which the return oil is supplied through an oil return collective piping system 44. In the first of the chambers produced by this subdivision, by means of partitions 42, there occurs a sedementation of coarser residues as well as the removal of impurities floating to the top through buoyancy. In the last chamber, the oil is tempered by means of heating elements and additional purification occurs by means of plate separators. The entry supply is caused by means of pumps 45 which supply the oil entrance line 47 through filters 46. The receptacle $40_0$ is inserted into this collective line leading to the user, namely the individual lubricating points $48_1$ to $48_n$, with the temperature sensor $21_0$ being added which controls the temperature compensated capacitance measuring device $38_0$ together with the electrodes of the receptacle.

The oil supplying the lubricating points is recovered by the collection bowls $49_1$ to $49_n$ and supplied to the oil return collective line through return lines $50_1$ to $50_n$ Receptacles $14_1$ to $14_n$ are respectively inserted into the individual return lines, whose electrodes control the associated temperature compensated capacitance measuring devices $38_1$ to $38_n$. The results are supplied to a central control and memory unit 51 through lines depicted in broken dotted fashion which permits the selective presentation of measuring data in the associated display device 19. In order to obtain a better overall view, this display device is built in such a way that it can depict the chronological sequence of the measuring results within a predetermined period of time. It can be designed as a recording ribbon of a writing point recorder or as a picture tube of a monitor. In this manner, it is easy to depict different results in parallel fashion, if the recording device has appropriately differing color stylos and/or by sidewise shift which records the curves representing the results next to each other. Also, if a picture tube is utilized, several results can be depicted in a parallel fashion, by depicting them offset with respect to each other and/or in case a color picture tube is used by different colors and/or by differing curve shapes, whereby different curves can be achievable by rhythmic blanking of the cathode beam so that the print line can be differentiated in such a way that, for instance, one is recorded in full lines, while others have differing dots, broken lines or dotted-broken lines. The central control and memory unit permits the presentation of, for instance, the inlet concentration and appropriately parallel thereto the monitoring of the capacitance measuring devices assigned to the individual return lines. Through this, it not only becomes possible to rapidly localize the reasons, in case the water concentration rapidly rises in the supply line, since the capacitance measuring device is assigned to the return lines causing the rise of the water concentration by uncontrolled entry of water to permit the presentation of strongly increased concentration values. It is possible to determine the rise of the concentration already directly at its initiation, since the capacitance measuring device 38 assigned to the return line 50, causing the concentration increase by uncontrolled entry of water, indicates the increasing concentration immediately at its initiation, before these can be sensed in the oil receptacle 43 and thus can be acquired through the oil supply line 47 and thus cause any effect. Here also, additional optical and/or acoustic signal devices are appropriately assigned to the central control and memory unit 51, which trigger warning signals if maximum values are exceeded, and possibly also already at the occurrence of unexpectedly high values. The central control and memory unit is appropriately designed in such a way that it can store measured values over long time periods so that these can be retrieved any time in a reproducible manner. Furthermore, it has proved desirable to pick out the values to be respectively displayed in a selectably switchable manner so that, for instance, only one or certain preselected curves are displayed individually or in groups thus improving the overall view, while generally, for instance, all measuring points can be switched onto the display device 19 in parallel fashion. Furthermore, it has proven itself, for instance, also to maintain the time interval to be displayed on the abscissa to be adjustable or changeable.

In all these cases, a monitoring device for an oil circulation system is created, which permits water content measurements to be accomplished continuously and without gaps and with a modest expense and to trigger a warning signal if insurprising and/or dangerous high values occur, whereby the multitude of measurements simultaneously permits localization of possibly having occurred malfunctions, so that inspection or repair or down time caused by an excessive water content can be held to a minimum.

While specific embodiments of the invention have been shown and described in detail to illustrate the application of the inventive principles, it will be understood that the invention may be embodied otherwise without departing from such principles.

What is claimed is:

1. Apparatus for monitoring the mixture ratio of two different liquids having substantially different dielectric constants comprising receptacle means having said liquids therein, said receptacle means comprising two electrodes lying opposite each other and capacitance measuring means connected with said electrodes and measuring the capacitance existing between them, wherein said receptacle means is provided in a collective entrance line for a liquid to be monitored, and wherein said receptacle means comprise a plurality of receptacles and wherein in a first line a first receptacle of said receptacles is provided having a capacitance measuring device with an average value generator located downstream thereof, and that the other of said receptacles are provided in additional lines whose capacitance values determined by said capacitance measuring means can be compared with those existing at the output of an average value generator.

2. Apparatus according to claim 1, wherein said receptacle means include a sensor of a temperature transmitter, output signals being supplied to a function imager located downstream and correcting data of said capacitance measuring means.

3. Apparatus according to claim 1, wherein subtractors are positioned downstream of outputs of said capacitance measuring means which reduce the capacitance values supplied to them by the values existing at the output of said average value generator.

4. Apparatus according to claim 1, wherein a visual display is effected through recording measuring instruments.

5. Apparatus according to claim 1, wherein visual displays occur through picture screens of cathode ray tubes, whereby in the case of multiple displays the values of different capacitance measuring devices of said capacitance measuring means are displayable by different colors on a color picture screen and/or by different periodic interruptions of the cathode ray as dotted lines upon the picture tube.

6. Apparatus according to claim 5, further comprising a central switching and memory unit arranged upstream of the instrument exhibiting said picture screen which permit the presentation of the measured values collectively in their entirety and/or selectively selected measuring points and/or measuring intervals.

7. Apparatus according to claim 1, wherein said capacitance measuring means comprises a generator supplying an integrator, and that the steepness of the integrator can be influenced by the capacitance occurring between said electrodes.

* * * * *